United States Patent [19]
Metz et al.

[11] Patent Number: 5,827,499
[45] Date of Patent: Oct. 27, 1998

[54] DETERMINING EFFECTS OF PSYCHOACTIVE COMPOUNDS ON THE BRAIN USING POSITRON EMISSION TOMOGRAPHY

[76] Inventors: John T. Metz, 2843 W. Rascher, Chicago, Ill. 60625; Malcolm D. Cooper, 612 C S. Laflin St., Chicago, Ill. 60607

[21] Appl. No.: 522,685

[22] Filed: Sep. 1, 1995

[51] Int. Cl.$^6$ .......... A61K 51/04; A61K 31/445; A61K 31/44; A61K 31/135; A61K 31/045

[52] U.S. Cl. .......... 424/1.73; 424/1.61; 514/322; 514/356; 514/649; 514/651; 514/724

[58] Field of Search .......... 514/649, 651, 514/724, 322, 356; 424/1.73, 1.61

[56] References Cited

PUBLICATIONS

Baxter et al, *Biological Abstracts*, vol. 94, Abstract No. 125570, 1992.
DeWilt et al, *Biological Abstracts*, vol. 90, Abstract No. 68450, 1990.
Volkow et al, *Biological Abstracts*, vol. 90, Abstract No. 81769, 1990.

*Primary Examiner*—William R. A. Jarvis
*Attorney, Agent, or Firm*—Andrus, Sceales, Starke & Sawall

[57] ABSTRACT

A method of determining the effects of administering a psychoactive compound, such as a drug, on a patient's brain using imaging techniques with position emission tomography (PET) is disclosed. The method measures cerebral metabolism before and after administering the compound, and employs a behavioral clamp to control behavioral influences on the patient's brain after administration of the compound. The method also includes transportation of image data into standard computer space and statistical procedures for volumetrically determining areas of treatment effects.

12 Claims, 3 Drawing Sheets

(3 of 3 Drawing Sheet(s) Filed in Color)

DETERMINING EFFECTS OF PSYCHOACTIVE COMPOUNDS ON THE BRAIN USING POSITRON EMISSION TOMOGRAPHY

BACKGROUND AND SUMMARY OF THE INVENTION

The present invention relates to a method of measuring the effects of psychoactive compounds, such as pharmaceutical drugs, and more particularly to a method of determining the effects of administering a psychoactive compound on a patient's brain using imaging techniques with positron emission tomography (PET).

Positron emission tomography (PET) is a radiotracer based method for producing images that quantitatively represent some biochemical property of the body (or portions of the body). In relation to this work, our use of PET is confined to metabolic imaging of the brain. Although other methods are often used, the aspect of PET that is relevant to this particular work involves 2-fluoro-deoxyglucose (FDG) as the tracer in studies of cerebral metabolism and oxygen-15 labelled water (O15) as the tracer in studies of cerebral blood flow. In general, FDG is used to estimate the rate of metabolism of glucose in different parts of the brain (Sokoloff, 1985) and provides data that represent integrated metabolic activity over a 20–40 minute period. O15 studies determine rate of blood flow in different parts of the brain with an integration period of 40–60 seconds. Given the different temporal demands of the two kinds of tracers, metabolic studies with FDG reveal relatively long-lasting effects or conditions (such as pathologies), whereas O15 studies are more sensitive to rapid, transient activity (such as sensory processes or cognition).

The problem that we are interested in is to determine how certain external treatments affect cerebral metabolism. The external treatments are usually drugs, but other interventions would be faced with the same considerations. The basic paradigm which we use to study external treatments is conceptually very simple: 1) measure metabolism without any treatment; 2) apply the treatment; 3) measure metabolism again;

and 4) determine whether the measurement at step 3 is statistically different from the measurement at step 1. In actuality, there are a number of experimental difficulties that must be dealt with before this paradigm can be applied.

First of all, it is important to realize that all images provided by PET reflect every influence on the brain at the time of a study. All perceptions, movements, thoughts, and moods, as well as vegetative functions, have correlates in brain metabolism and blood flow, and these factors, which are always present, may obscure effects due to treatment. Even more critically, these factors may change in unknown ways in response to the treatment and hence the extent of their influence on observed metabolism becomes unpredictable. It can, therefore, be difficult to determine which features of an image are due specifically to the experimental treatment and which are secondary, due to some other change that occurs because of the treatment. The objective of much of our work has been to develop ways of processing PET images so that we can more easily identify metabolic effects that are due to a specific external treatment.

Some of our earliest work involved the recognition that the condition of subjects at the time of a study might vary from subject to subject or even within the same subject at different times (Levy et al., 1987). Variation in the testing condition thus could make it difficult to isolate differences introduced by an external treatment.

Accordingly, we have developed an appropriate standard condition for testing subjects. This condition is the visual monitoring task (VMT). The VMT requires that subjects watch a screen on which is projected either a bright light or a dim light. The lights are easily distinguished from each other. One light flashes at a varying interval of 4 to 7 seconds. The two lights are equally probable. We ordinarily test subjects for 3 to 4 blocks (96 total trials each block, about 10 minutes per block) with a slight break between blocks. Subjects are instructed to press a button every time the dim light flashes and to ignore the bright flashes (a very subtle point: the natural tendency is to respond to the bright light which is more salient; by making the dim light the target a slight increase in difficulty is introduced). A computer measures reaction time (RT) to each button press (expressed as median RT per block) and whether the press was correct (a dim light), false alarm (a bright light), or missing (dim light flashed but subject did not press the button). In some situations, the VMT includes a feedback system so that subjects could see how fast their RT's to target flashes were. This produces more consistent RT's (lower variance). The VMT differs from other tasks that are occasionally used in PET studies (Buchsbaum et al., 1992; Hazlett et al., 1993) in that it is extremely simple and undemanding—subjects can do this task even if they are very young, very old, or slightly affected by a drug. At the same time, successful performance of the task precludes extraneous mental activity.

In early drug/PET work, a common procedure was to use a fairly large dose of a drug in order to produce the largest practical metabolic or blood flow "signal". We, however, immediately recognized that this would create a problem. Some of the drugs that we were planning to study (e.g., ethanol, diazepam) would likely incapacitate subjects to the point where they would not be able to perform the VMT adequately. However, we were convinced that any dramatic change in behavior as a result of taking a drug would be impossible to interpret (as an extreme example, subjects who are sleeping after a drink of ethanol should not be compared to waking subjects—there would undoubtedly be differences, but these would not be due to the drug but the condition of the subjects).

Therefore, use of the VMT as part of our drug studies necessarily limits the dose of some drugs that can be studied. Thus, we chose to sacrifice a large but confounded signal in order to get a small but clean signal.

We also recognized that some subjects became very competitive while performing the VMT, visibly trying to get the lowest possible RT. We thus recognized that the demands of the VMT affected different subjects differently and perhaps would 10 affect them differently under various drug conditions.

Therefore, (and as now used in the OMEI process) we eliminated the RT feedback. Instead, we explicitly adopted an exclusion criterion: any condition on which RT is not stable (operationally defined as deviating by more than 10% from a reference condition) must be discarded. Similarly, any subject who does not perform with at least 95% accuracy (combined hits and correct rejections) must be omitted. Because subjects are confined to a relatively narrow range of behavior, we refer to this phase of the process as a "behavioral clamp."

The VMT provides fairly good control of subject's overt behavior and even of their inner behavior (thinking). However, it does nothing to control mood, another variable that could be different under reference and drug conditions, but as with sleep in the behavioral domain, it would be incorrect to attribute metabolic changes to a drug. In order to minimize the contribution of mood to metabolic changes that we would observe, we introduced into the PET experiments a standard test procedure. We administer the Profile of Mood States—POMS (McNair et al., 1971), a brief self-administered adjective check list that has been shown to be sensitive to drug effects (de Wit et al., 1985; de Wit et al., 1986). POMS scale scores are determined before and after the placebo and before and after the treatment. The difference between these scores indicates how much mood changed as a result of the treatment, as opposed to changes due to fatigue, boredom, etc. We recognize that mood is difficult to control, but by measuring it we can incorporate significant mood changes into our interpretation of metabolic changes. Where practical, this often involves separating subjects who change in mood from those who do not (or who change in the opposite direction) and creating different images of metabolic change for each group.

Having deliberately chosen to deal with relatively small signals due to our external treatment, we were next faced with the problem of detecting those signals. The standard method of dealing with metabolic images in PET studies (prior to OMEI) consists of drawing anatomical regions of interest (ROIs) on the slices that the scanner provides; this is done under both reference and treatment conditions. In its more recent form (Gur et al., 1995a), the ROIs are drawn on each subject's MRI then applied to the PET images that are spatially correlated (in three dimensions) with the MRI. In either form, this method is relatively insensitive to small changes in brain metabolism (Fox, 1991).

1. Even with the best positioning techniques, there will be slight differences in positioning of subjects on different occasions. In the case of repeated O15 scans we have even noticed significant changes in subject positions (up to 5mm) within the same session; this problem, of course, is exacerbated when metabolic studies occur in different sessions on different days. This means that slices of the brain in one condition will not correspond exactly to ROIs from another condition.

2. The problem of different slices is even more serious when looking at different subjects since anatomical differences will prevent definition of identical ROIs.

3. Even the best drawing of ROIs cannot perfectly define all regions identically in all subjects. Not only will experimenter error and biases be present, but differences in anatomical features will cause some variation in definition of ROIs.

4. Any ROI must necessarily include relatively unresponsive subregions (e.g., white matter, portions near boundaries of ventricles or external surfaces that incorporate different partial volume effects).

5. True physiological effects will often not fill an entire ROI, no matter how small the ROIs may be. 6. Because the ROIs are defined independently of each other, physiological effects that cross ROI boundaries may fail to show up in any one ROI even though an effect may be relatively large.

The first five of these considerations serve to add "noise" to the signal that we would be trying to detect; the sixth effectively reduces the size of a signal even further. Nevertheless, to our knowledge all PET metabolic studies to date, including our own (de Wit et al., 1988; de Wit et al., 1991), have used this basic approach. This approach, as we and others demonstrated, can work in the sense of demonstrating robust effects. When combined with the behavioral clamp procedure, this approach can certainly provide interpretable metabolic images. At worst, it would only require the studying of a sufficiently large number of subjects to determine effects of any drug (this, of course, can be practically impossible, given the cost of PET studies).

Coincidentally with these metabolic studies, however, others were conducting studies of cerebral blood flow with O15. In these studies it was early recognized that small signals were involved and therefore more sensitive analytic approaches were required. Such approaches were developed in several laboratories (Fox et al., 1988; Fox and Mintun, 1989). Underlying these more sensitive methods were two conceptual shifts from the standard procedure.

The first as a recognition that PET was providing true physiological data, not anatomical data (Fox, 1991). It stands to reasons, therefore, that the physiological data itself would be more sensitive than a priori anatomical features. In this sense, these methods were "data driven". The second shift was an effective realization that the slice-based data provided by PET scanners are estimates of true metabolic activity in the brain. Alternative ways of estimating metabolic activity can be validly employed. Briefly, the PET brain could be conceived of as a whole, relatively smooth volume rather than a set of discrete slices. Of course there are assumptions and limitations in this volumetric approach, but they are not necessarily worse than those of the slice-based approach. Most important, the volumetric approach allows for different kinds of data manipulation in experimental settings.

Specifically, estimates can be made for the metabolic value at every point in the brain and the brain can all be transformed into a standard three-dimensional space. Several different methods have been developed for estimating all points in the brain volume. Basically, they all involve interpolation from measured slice centers to every point in the vicinity of the slice center. At present, only linear interpolations have been employed but other methods are being researched (Lin et al., 1988; Lin et al., 1989). Likewise, the transformation problem has been solved several times (Evans et al., 1987; Fox et al., 1988; Evans et al., 1991). Investigators in our laboratory have been most successful in developing the procedure for spatially correlating PET and MRI or x-ray CT images (Pelizzari et al., 1989). While not essential, this step is one more way of reducing noise due to imprecision of the spacial transformations. Although we have preferred ways of treating our data, we recognize that there are a number of comparably good techniques. The critical point for the OMEI procedure is that volumetric handling of the data with transformation into standard space is an essential part of the procedure.

The present invention involves brain-behavior relationships and methods for measuring them using imaging techniques with positron emission tomography (PET). In particular we are concerned with methods that measure quantitative changes in blood flow, metabolism and ligand localization and binding. More specifically we have been involved with elucidating the effects of drugs and other psychoactive compounds with abuse potential and cognitive challenges concerning attention and memory. We have effected a method which enables us to measure regional metabolic changes in the brain and associated mood changes from a single-dose drug challenge in a controlled behavioral state.

The method presents a new perspective inasmuch as it reveals the end-pathway of the psychoactive compound's effect by the metabolic process involved. Thus, it demonstrates those regional brain areas which effect the functional changes induced by the action of the drug or psychoactive compound. Further, it can characterize the metabolic changes in quantitative terms as to whether the regional metabolic change is relatively increased or decreased. This "end-effect" measure is particularly important since we have shown it is quite distinct from the site of localization of the radiolabelled drug, its ligand-binding characteristics or the neurotransmitter systems involved.

A series of studies indicate this is an effective in vivo means of characterizing drug effects and thus can provide a new and valuable approach to drug development. Specifically, we see an application in devising effective and efficient strategies in the clinical phases of development; not least from the ability to rapidly obtain a measure of effectiveness by direct comparison with already characterized and available compounds. We believe the method can be applied in all three clinical phases of drug development—safety, efficacy and dosage. It can also be a means to determine the effects of drug combinations and examine synergy or inhibition. Our special interest is in psychoactive compounds that effect mood and behavior and their associate neuropsychiatric disorders. However, the approach is also applicable in drugs targeted to broader range of syndromes and disorders in the brain. Similarly, we recognize the potential in determining drug side-effects including CNS changes arising from non-brain targeted pharmaceuticals.

In terms of drug development, the efficiency of the method is an outstanding attribute. Significant measures may be obtained from as few as eight subjects and comparative results provided with a matter of weeks. It is amenable to many variations in the drug testing procedure including measures of acute and chronic effects and alterations in dosage, scheduling and delivery. It will provide an important measure of drug effect since for the first time it will be possible to relate dosage and drug plasma levels to a quantitative measure of regional changes in the central nervous system. Similarly, when these measures are related to parenchymal organ function of blood biochemistry, then toxicity versus therapeutic efficacy can be quantitatively appraised.

These considerations indicate that the method can have a significant impact upon both the cost and rate at which new drugs can be developed and brought to market. Archived compounds can be efficiently re-evaluated and, perhaps most importantly, it will increase the number and type of new compounds that can be applied in the therapy of diseases affecting the brain.

The method involves (1) measuring cerebral metabolism of a patients' brain prior to any treatment with a psychoactive compound; (2) administering the psychoactive compound to the patient; (3) controlling behavioral influences on the patient's brain by subjecting the patient to a behavioral clamp; (4) measuring cerebral metabolism of the patient's brain after administering the psychoactive compound and during the behavioral clamp; and (5) determining any differences between cerebral metabolism prior to administering the psychoactive compound and cerebral metabolism after administering the psychoactive compound.

BRIEF DESCRIPTION OF THE DRAWINGS

The file of this patent contains at least one drawing executed in color.

DISCLOSURE OF THE INVENTION

Figure 1:
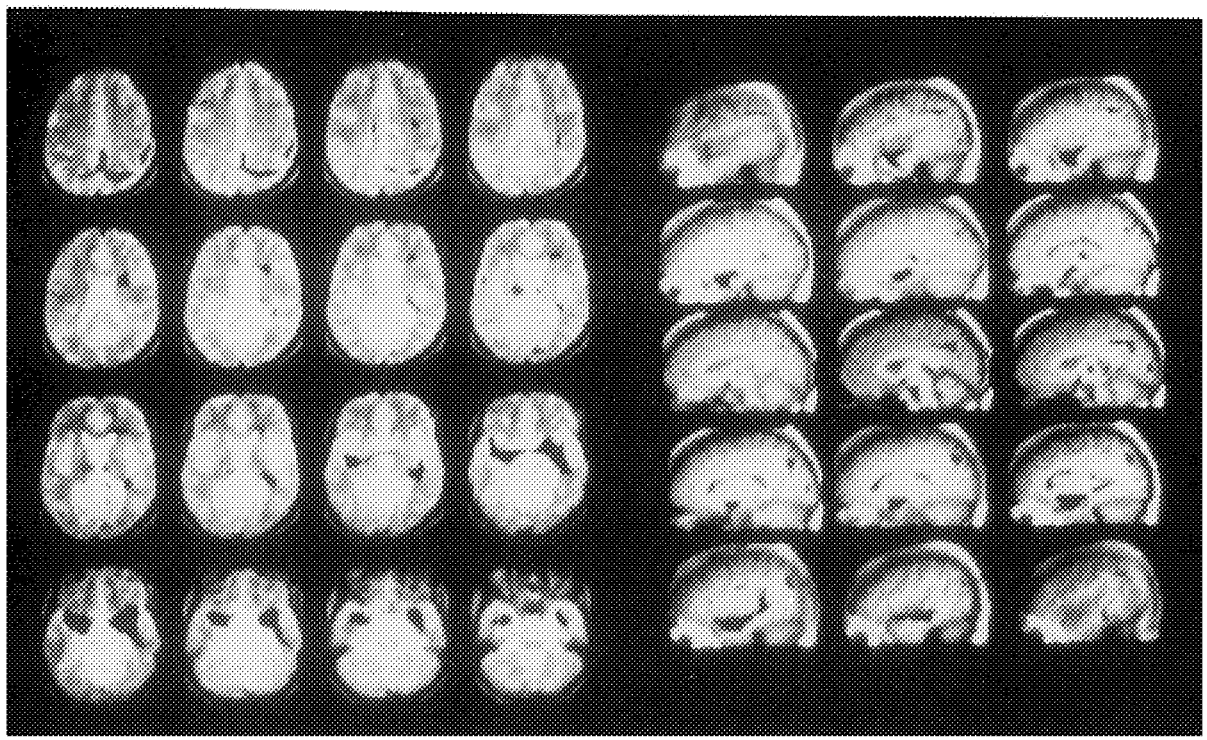
FIG. 1 illustrates a series of PET images superimposed on MRI brain images demonstrating fluoxetine effects on cerebral glucose metabolism.

The Optimization of Metabolic Effect Identification (OMEI) procedure disclosed herein uses positron emission tomography (PET) for the purpose of identifying regions of the brain that are affected by an external treatment. The external treatment will usually be a pharmacological treatment but the procedure is not limited to this type of study and may be employed to determine the effects of any psychoactive compound on a patient's brain. For example, pimozide, ethanol, fluoxetine, perfumes, taste or flavoring compounds, etc. are all examples of psychoactive compounds. The procedure is effective because it reduces the influence on metabolism of effects not directly due to the treatment being studied and because it uses the most sensitive available methods for detection of areas that change in metabolism because of the treatment.

The procedure consists of four steps:

1. Collection of Metabolic Data: Two or more PET sessions are conducted for every subject. In each session, fluoro-deoxyglucose (FDG) is used as the tracer to measure regional cerebral metabolism of glucose according to standard methods (Phelps et al., 1979; Reivich et al., 1979). One of these sessions is designated as the reference session. In most cases, the reference session includes the administration of an inert treatment (placebo); the other session(s) include the administration of a treatment such as a drug (or drugs) which is assumed or hypothesized to affect the brain. Ideally, the treatments should be administered with the placebo in a double-blind, counterbalanced fashion at a time prior to administration or of the dose of the treatment (within limits—see below) permits determination of time-activity or dose-response curves. PET data can be collected in any convenient units (e.g. absolute units of glucose per unit tissue per unit time, or normalized relative to whole brain mean and standard deviation), although the ultimate interpretation will be affected by the choice of units.

2. Control of Behavioral and Subjective Influences on the Brain: In each PET session the subject performs a behavioral task which has one or more measurable variables. The behavioral task is chosen so as to maintain subjects in a standard and stable condition throughout the period of FDG equilibration (20–40 minutes after injection). The task must be capable of being performed at comparable levels by all subjects with or without the treatments that may be used in the study. Thus, the task should be relatively simple, requiring a non-stressful level of attention with no opportunity for developing a productive strategy. The measurable variables associated with the task are used to define criteria for a valid study only subjects who perform the task at a specified level are included in subsequent analyses. Because subjects are behaviorally restricted to a relatively narrow range of responses, we refer to this step as a "behavioral clamp". Implicit to this approach is a recognition that only certain levels of the treatment can be studied by this method. For example, a dose of a drug which invariable produces sleep or uncontrollable agitation could not be studied. In our usual application, the clamp consists of visual monitoring task (VMT) is which the subject is asked to press a button held in one hand every time a dim light is flashed on a screen but to ignore an equally probably and easily discriminated bright flash. Bright or dim lights flash randomly for 250 msec at varying intervals between 4 and 7 seconds. Arbitrarily, we set the validity level at 95% accuracy with reaction times varying in experimental conditions by no more than ±10% from the reference condition for each subject.

The task should also minimize subjective variables such as extraneous ideation, motivation, anxiety, etc. In part, this is accomplished by the choice of a behavioral clamp which is sufficiently but not excessively demanding; this is verified by the overall stability of performance by subjects across a wide range of treatments and subjects. In addition, some subjective variables can be quantified by standard psychological instruments. We administer the Profile of Mood States (POMS) (McNair et al., 1971) before and immediately after the equilibration period. If there is a significant group difference as a function of treatment, the subjects are divided into subgroups so as to facilitate attribution of image differences to the measured subjective differences. Thus, there are two components to this step: clamping the behavior and measuring mood.

3. Transposition of Image Data into Standard Computer Space: Metabolic image data collected from each subject are transposed into a standard anatomical space. This involves shifting, shrinking or expanding, and rotating PET image sets so that any point within the image-brain of one subject corresponds (in x, y, and z coordinates) to the same point in the image-brain of that subject under different conditions and to the same point in the image-brains of all other subjects. Several methods could be used to achieve this. We use a set of standard anatomical landmarks which can be identified in each three dimensional image-brain. The landmarks are then adjusted to correspond to their location in the Talairach atlas (Talairach and Tournoux, 1988). This process is facilitated by the collection of anatomical image-brain with the metabolic image-brain in computer space. We use the method of Pelazzari and colleagues, which was developed in our laboratory (Pelizzari et al., 1989); other methods could also be used. The landmarks are then identified in the anatomical image-brain, applied to the metabolic imagebrain, and transformed into the Talairach space.

4. Detection of Areas of Treatment Effects: A number of methods can be used to distinguish areas of the brain that show marked differences between the treatment conditions. We use a modification of statistical parametric mapping (Friston et al., 1991) in which within-subject t-tests are performed at each voxel in the standardized image-brains for each condition compared to the reference condition. The level for reporting differences is set depending on the requirements of the study. Simpler analyses, such as subtractions of the treatment mean images from the reference mean image can be used for preliminary analyses.

We claim a unique contribution especially for the development of step 2. The other steps are widely employed and accepted in the PET literature. We also claim the first recognition of the usefulness of the steps in combination as applied to the problem of evaluating the effects of an external treatment on cerebral metabolism.

The result of this procedure is to improve the ability to detect changes in neuronal energy consumption that can be attributed to an external treatment. The procedure does this by reducing the influence on metabolism of extraneous factors (i.e., those factors not specific to the treatment or secondary to the treatment) which would otherwise provide metabolic changes greater than those attributable to the treatment itself. Step 2 (Behavioral control), specifically, minimizes behavioral and subjective influences on metabolism. Step 3 was originally developed for use in PET studies of cerebral blood flow under conditions of sensory or cognitive activation. The merits of this approach in detecting physiological changes compared to the anatomical based methods which are the alternative "state of the art" have been discussed in the literature (Fox, 1991).

The location of metabolic changes which we have noted with this procedure do not necessarily correspond to known locations of receptors for the drugs that we have tested. Instead, they correspond to regions of maximal metabolic change due either to direct or indirect effects of the treatment.

Example 1

This study was conducted to determine the effects of oral administration of 40mg of fluoxetine, an agent which inhibits re-uptake of 5-HT, on CMRglu, as measured by positron emission tomography (PET) using ($^{18}$F)-2-deoxyglucose (FDG) in healthy human subjects.

Materials and Methods

Subjects: Four healthy control subjects were studied. Five potential subjects were screened for personal psychiatric history using the SCID-NP[5] and a clinical mental status examination. They were screened for mental illness with a history and physical examination. Potential subjects were excluded if they had Axis I disorders, substance abuse, alcohol abuse, or significant medical illness, and one was excluded because of a previous episode of major depression. None of the subjects who underwent the full procedures had taken psychotropic medication. Three of the subjects were male and one was female. The age of the subjects ranged from 20 to 39 years.

Procedures:

All PET studies were performed at the Franklin McLean Memorial Research Institute of the University of Chicago using a 3-ring PETT VI scanner. Each subject participated in two PET sessions. Subjects abstained from beverages containing sugar or caffeine and food for at least 4 hours preceding each study. Fluoxetine (40 mg) or matched placebo was administered orally in a double-blind, counter-balanced manner between 11.00 h and 13.00 h. At each session, the subject was positioned in the PETT VI in such a way that slices parallel to the orbital-meatal plane were obtained. A laser beam apparatus and custom-made plastic face mask assured precise and reproducible positioning. A transmission scan was performed in each session for attenuation correction. Intravenous catheters were inserted in each arm for blood sampling and for injection of the radioactive tracer.

Ninety minutes after administration of fluoxetine or placebo, subjects were repositioned in the PET scanner and a visual monitoring task (VMT) was initiated. The task assured a stable behavioral condition at the time of testing. Each subject was asked to press a button with his or her right thumb every time a dim light (50% of trials) was presented on a screen mounted in front of him or her and was asked to ignore every bright light (50%). The lights were presented under computer control at random intervals ranging from 4 to 7 sec. Each subjected completed four blocks of 96 trials each (approximately min per block). Subjects also completed the Profile of Mood States (POMS) before the capsule and 20 min after injection of FDG.

FDG (6.0–7.5mCi) was administered 30 sec after the initiation of the visual monitoring task and static scanning commenced 40 min later for a period of 14 min. Five simultaneous planes were obtained with an interplane separation of 14 mm. Subjects were then repositioned by moving the subject chair of acquisition of an additional five slices in static mode to more full sample the whole brain. In-plane resolution of PETT VI is 8mm at full width maximum.

Data Analysis:

PET images were reconstructed using standard methods.

Slices from the two scanning positions were combined into a single volume for each subject. Average CMRglu was estimated as the mean of all slices, excluding voxels having 60% or less of the maximum metabolic rate (assumed to be ventricles, white matter, and non-brain tissue). Average global CMRglu was compared between placebo and fluoxetine scans using the paired two-tailed t-test.

All voxels were normalized and expressed as a z-score value relative to the whole scan mean and standard deviation of gray matter voxels. PET volumes for each subject were spatially correlated across the two conditions using the surface-fitting technique developed in our laboratory.

PET volumes were also anatomically normalized, i.e., each subject's images were expanded, contracted, rotated, or shifted into a standard volume using the coordinate system of the Talairach atlas, we first identified a set of landmarks which were used to proportionally adjust the entire PET volume into "Talairach space". In Talairach space, the PET slices were linearly interplated between each measured slice to provide better localization of anatomical features.

In the Talairach volumes, two-tailed paired t-tests were performed comparing each voxel from placebo condition to each voxel after fluoxetine. Paired t-tests were used because each subject was tested in each condition. A t-value of 3.2 closely approximated statistical significance for 3 degrees of freedom. To adjust for the large number of voxels studied, we only considered regions significant if a large number of adjacent voxels had t-values greater than 3.2 or less than −3.2. Determination of localization of areas of increased or decreased metabolism were performed by displaying significant voxels in color overlaid on a gray scale MRI.

Results:

Average global CMRglu was not significantly different between placebo ($8.93 \pm 0.96$ mg 100 $g^{-1}min^{-1}$) and fluoxetine scans ($8.22 \pm 0.86$ 100 $g^{-1}$ ˉ, paired t=0.82, df3, p<0.48). Inspection of the t-test images revealed that two areas had marked changes in relative glucose metabolism. Most prominent was a bilateral C-shaped region consisting of amygdaloid complex, hippocampal formation, and ventral striatum which showed decreased relative glucose metabolism. A smaller area centered in the right superior parietal lobe (Brodmann area 7) showed increased relative metabolism (FIG. 1).

There were no systematic effects of fluoxetine on reaction time or accuracy on the VMT (median reaction time $571 \pm s.d.$ 125 ms after placebo, $553 \pm 64$ msec after fluoxetine, t=−0.78; $91.7 \pm 14.6\%$ correct after placebo, $96.4 \pm 3.2\%$ correct after fluoxetine, t=0.82). There were no differences in subjective effects as measured by the POMS.

Discussion:

FIG. 1 illustrates statistical maps of voxel-by-voxel repeated measures t-tests for the data obtained after subjects had received fluoxetine and placebo. PET images are superimposed on a normal MRI image in Talairach coordinate space, thresholded to show only (values greater than 3.2 (red) or less then −3.2 (blue X)(p<0.05). Red areas show regions in which the fluoxetine condition had greater relative metabolism than placebo; blue areas are regions in which the fluoxetine condition had less relative metabolism than placebo. In each axial slice, the front of the brain is at the top, the left side of the brain is to the left. Each successive slice (from left to right, then top to bottom) shows progressively lower slices in brain, beginning at Talairach coordinates approximately 3.4 cm above AC-PC line; slices are approximately 4.0 mm apart. Sagittal slices begin at the far left of the brain and proceed from left to right, top to bottom in approximately 6.5mm steps through the midsagittal plane (middle slice in second row) to the far right side. Administration of fluoxetine led to a decrease in CMRglu in bilateral amydeloid complex, hippocampal formation, and ventral striatum and an increase in metabolism centered in the right superior parietal lobe (Brodmann area 7).

Example 2

In this study we investigated the brain's response to the psychoactive compound pimozide. Subjects were tested under behavioral conditions substantially identical to the procedures described in Example 1, except pimozide was administered instead of fluoxetine.

Figure 2:
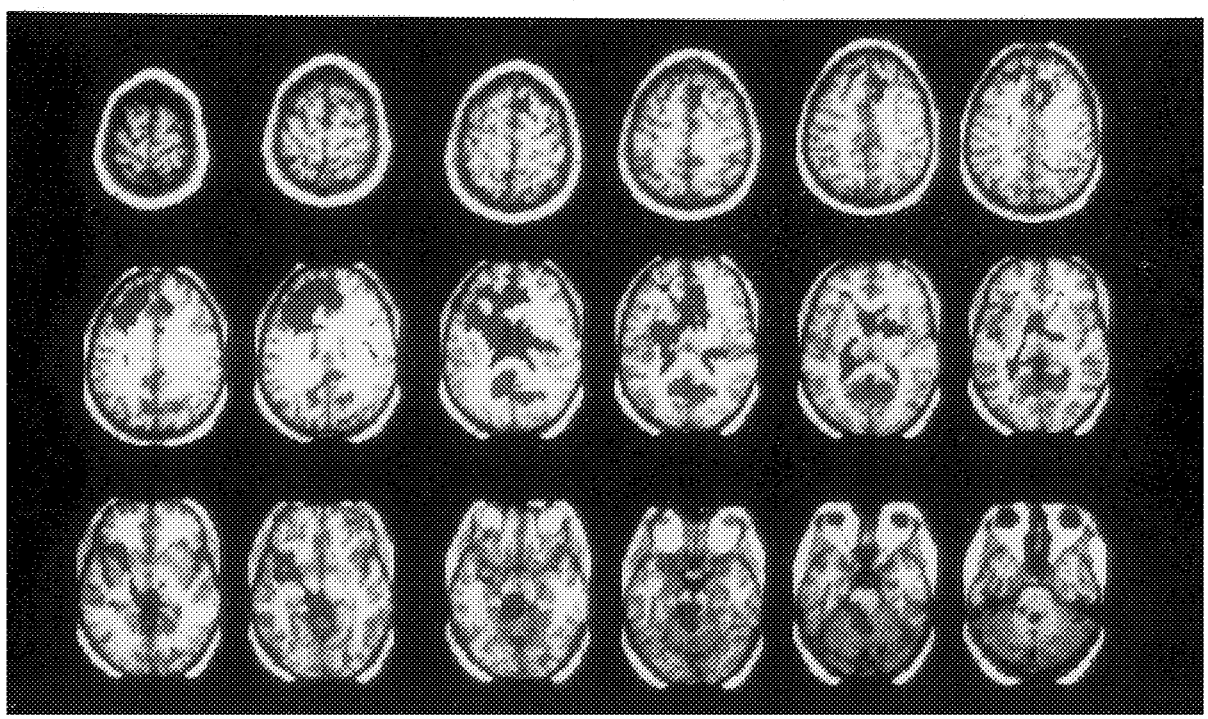
FIG. 2 illustrates a series of PET images superimposed on MRI brain images demonstrating pimozide effects on cerebral glucose metabolism.

FIG. 2 shows changes in rCMglu demonstrating the effects of pimozide.

Example 3

In the present PET study we tested subjects to investigate individual differences in response to ethanol. Subjects were tested with placebo (tonic water) and with a moderate dose (0.5 g/kg) of ethanol under comparable behavioral conditions substantially in accordance with the procedures described in Example 1.

Figure 3:
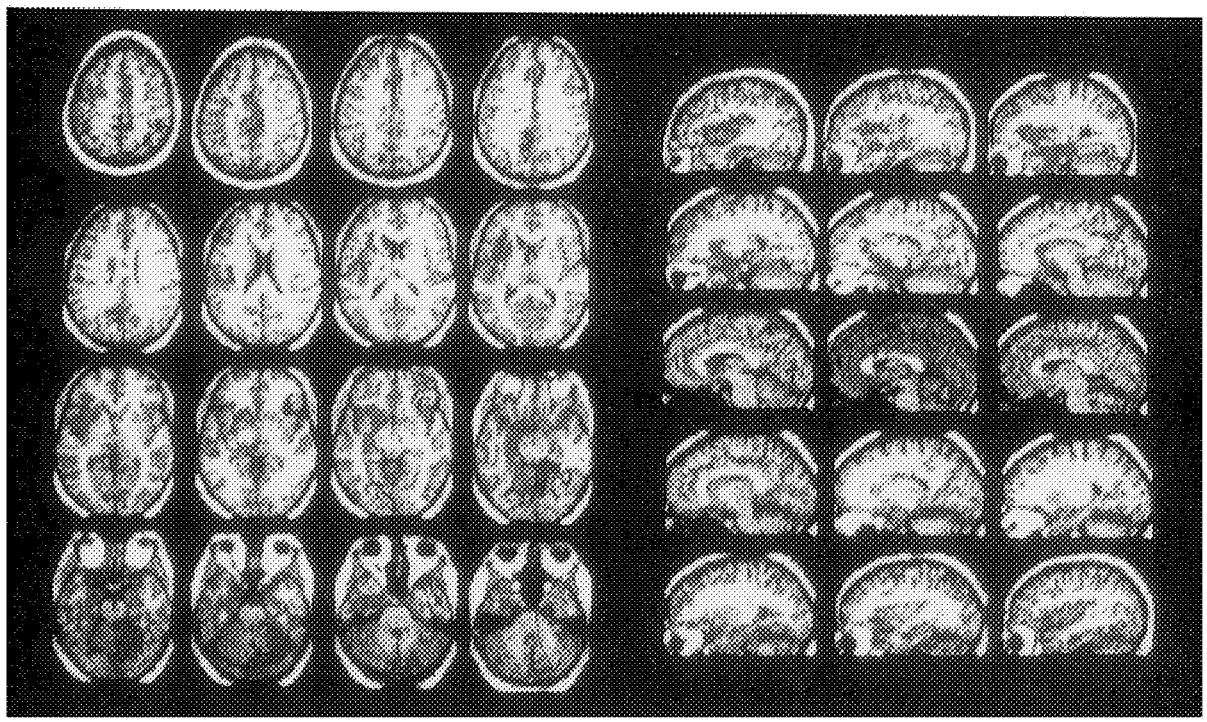
FIG. 3 illustrates a series of PET images superimposed on MRI brain images demonstrating ethanol effects on cerebral glucose metabolism.

FIG. 3 shows changes in rCMglu demonstrating the ethanol effects. The most striking effect was a widespread increase in rCMglu in the left hemisphere. Other areas affected were in the frontal and temporal lobes, basal ganglia, and limbic system.

Example 4

In this study we investigated the brain's response to the psychoactive compound nimodopine. Nimodopine (0.5 g/kg) or placebo (mix alone) was administered in a 250 ml beverage in lime juice and tonic water to be consumed in five minutes. All other behavioral conditions were substantially identical to the procedures described in Example 1.

The data appear to show decreased metabolism in the cingulate gyrus and/or left posterior temporal lobe with patchy increased metabolism in the superior portion of the cerebellum and/or interior portion of the occipital lobe.

I claim:

1. A method of evaluating the effects of administering a psychoactive compound to a patient on the patient's brain, comprising the steps of:

measuring cerebral metabolism of a patient's brain prior to any treatment with a psychoactive compound;

administering a psychoactive compound to the patient;

controlling behavioral influences on the patient's brain by subjecting the patient to a behavioral clamp, said behavior clamp comprising a procedure that (a) maintains the patient in a standard and stable condition throughout a period of cerebral metabolism of said psychoactive compound;

(b) is capable of being performed by the patient at comparable levels prior to as well as subsequent to administration of said psychoactive compound;

(c) requires a non-stressful level of attention with no opportunity for the patient to develop a productive strategy;

(d) includes measurable variables capable of defining desired criteria: and (e) minimizes subjective variables including extraneous ideation, motivation and anxiety;

measuring cerebral metabolism of the patient's brain after administering the psychoactive compound and during the behavioral clamp; and determining any differences between cerebral metabolism prior to administering the psychoactive compound and cerebral metabolism after administering the psychoactive compound.

2. The method of claim 1 wherein the compound administered is fluoxetine.

3. The method of claim 1 wherein the compound administered is ethanol.

4. The method of claim 1 wherein the compound administered is pimozide.

5. The method of claim 1 wherein the compound administered is nimodopine.

6. The method of claim 1 wherein the step of measuring cerebral metabolism prior to any treatment utilizes positron emission tomography.

7. The method of claim 1 wherein the step of measuring cerebral metabolism after administering the compound utilizes positron emission tomography.

8. The method of claim 1 wherein said behavioral clamp comprises a visual monitoring task performed by the patient.

9. The method of claim 1 further comprising the step of measuring a patient's mood both prior to and after administering the compound.

10. The method of claim 9 wherein the step of measuring a patient's mood comprises administering a standard psychological test thereto.

11. The method of claim 10 wherein said standard psychological test is a profile of mood states.

12. The method of claim 1 further comprising the step of comparing the cerebral metabolism after administering the compound to a reference cerebral metabolism.

* * * * *